(12) United States Patent
Jang et al.

(10) Patent No.: US 11,911,157 B2
(45) Date of Patent: Feb. 27, 2024

(54) APPARATUS AND METHOD FOR ESTIMATING TARGET COMPONENT

(71) Applicant: SAMSUNG ELECTRONICS CO., LTD., Suwon-si (KR)

(72) Inventors: Hyeong Seok Jang, Seoul (KR); Sung Hyun Nam, Yongin-si (KR); Sung Mo Ahn, Yongin-si (KR); Jun Ho Lee, Incheon (KR); Ho Jun Chang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 251 days.

(21) Appl. No.: 17/319,804

(22) Filed: May 13, 2021

(65) Prior Publication Data
US 2022/0280078 A1 Sep. 8, 2022

(30) Foreign Application Priority Data
Mar. 3, 2021 (KR) .................. 10-2021-0028122

(51) Int. Cl.
*A61B 5/1491* (2006.01)
*A61B 5/1455* (2006.01)
(Continued)

(52) U.S. Cl.
CPC .......... *A61B 5/1491* (2013.01); *A61B 5/1455* (2013.01); *G01K 11/12* (2013.01);
(Continued)

(58) Field of Classification Search
None
See application file for complete search history.

(56) References Cited

U.S. PATENT DOCUMENTS 6,943,883 B2 9/2005 Fodgaard
6,990,364 B2 1/2006 Ruchti et al.
(Continued)

FOREIGN PATENT DOCUMENTS

KR 10-2042864 B1 11/2019

OTHER PUBLICATIONS

Rinnan et al., "Review of the most common pre-processing techniques for near-infrared spectra," Trends in Analytical Chemistry, vol. 28, No. 10, Elsevier, 2009, pp. 1201-1222, (22 total pages).
(Continued)

*Primary Examiner* — Devin B Henson
*Assistant Examiner* — Matthew Eric Ogles
(74) *Attorney, Agent, or Firm* — Sughrue Mion, PLLC

(57) ABSTRACT

Provided is an apparatus for estimating a target component, the apparatus including a temperature controller configured to modulate temperature of an object, a measurer configured to measure a spectrum for each temperature of the object that changes based on the modulation, and a processor configured to obtain effective optical pathlength vectors corresponding to a temperature change based on the spectrum for each temperature of the object, obtain a representative effective optical pathlength based on the obtained effective optical pathlength vectors, and obtain a target component estimation model based on the obtained representative effective optical pathlength.

16 Claims, 10 Drawing Sheets

(51) Int. Cl.
*G16H 50/30* (2018.01)
*G01K 11/12* (2021.01)
*G16H 50/70* (2018.01)
*G05D 23/27* (2006.01)
*G05B 17/02* (2006.01)
*G16H 40/67* (2018.01)

(52) U.S. Cl.
CPC ............ G05B 17/02 (2013.01); G05D 23/27 (2013.01); G16H 50/30 (2018.01); G16H 50/70 (2018.01); *A61B 2560/0233* (2013.01); *A61B 2560/0431* (2013.01); *A61B 2562/0242* (2013.01); *A61B 2562/0271* (2013.01); *G16H 40/67* (2018.01)

(56) References Cited

U.S. PATENT DOCUMENTS

| | | | |
|---|---|---|---|
| 7,881,892 | B2 | 2/2011 | Soyemi et al. |
| 8,734,536 | B2 | 5/2014 | Beck et al. |
| 10,139,388 | B2 | 11/2018 | Sterenborg et al. |
| 10,761,101 | B2 | 9/2020 | Lee et al. |
| 2002/0084417 | A1* | 7/2002 | Khalil ............... G01N 21/49 250/341.8 |
| 2003/0166997 | A1* | 9/2003 | Chance ............... A61B 5/1455 600/322 |
| 2005/0192488 | A1 | 9/2005 | Bryenton et al. |
| 2009/0075324 | A1 | 3/2009 | Pettersson |
| 2018/0192929 | A1 | 7/2018 | Scheele et al. |
| 2020/0121244 | A1* | 4/2020 | Lee ..................... A61B 5/0002 |
| 2020/0158629 | A1* | 5/2020 | Jang .................... G01J 3/32 |

OTHER PUBLICATIONS

Sassaroli et al., "Comment on the modified Beer-Lambert law for scattering media," Institute of Physics Publishing, Physics in Medicine and Biology, Phys. Med. Biol. 49, Jul. 5, 2004, pp. N255-N257, (3 total pages).

Gardner, Craig M., "Transmission versus reflectance spectroscopy for quantitation," Journal of Biomedical Optics 23(1), Jan. 2018, (9 pages).

* cited by examiner

APPARATUS AND METHOD FOR ESTIMATING TARGET COMPONENT

CROSS-REFERENCE TO RELATED APPLICATION

This application claims priority from Korean Patent Application No. 10-2021-0028122, filed on Mar. 3, 2021, in the Korean Intellectual Property Office, the entirety of which is incorporated herein by reference.

BACKGROUND

1. Field

Example embodiments of the present disclosure relate to an apparatus and method for estimating a component of an object based on an absorbance spectrum.

2. Description of Related Art

Recently, research is conducted on methods of measuring bio-information, such as blood glucose, in a non-invasive manner using Raman spectroscopy or near-infrared spectroscopy (NIRS).

When temperature of an object is changed during spectrum measurement in a scattering medium, an absorption coefficient and a scattering coefficient are optically changed at the same time, and optical pathlength distribution is changed for each wavelength due to scattering. The change in absorption coefficient is mainly caused by a difference in refractive-index change of a medium and a scatterer due to a temperature increase, and the change in scattering coefficient is mainly caused by a change in absorption coefficient of water according to temperature.

In such changing environments, quantitative analysis of the object based on the general Beer-Lambert law has a limitation in that it assumes optical pathlength distribution at all wavelengths is equal.

SUMMARY

One or more example embodiments provide to an apparatus and method for estimating a component of an object based on an absorbance spectrum.

According to an aspect of an example embodiment, there is provided an apparatus for estimating a target component, the apparatus including a temperature controller configured to modulate temperature of an object, a measurer configured to measure a spectrum for each temperature of the object that changes based on the modulation, and a processor configured to obtain effective optical pathlength vectors corresponding to a temperature change based on the spectrum for each temperature of the object, obtain a representative effective optical pathlength based on the obtained effective optical pathlength vectors, and obtain a target component estimation model based on the obtained representative effective optical pathlength.

The temperature controller may include a heater configured to provide thermal energy to the object, and a temperature sensor configured to measure the temperature change of the object.

The temperature controller may be further configured to perform modulation one or more times within a predetermined temperature range.

The measurer may include one or more light sources configured to emit light of one or more wavelengths to the object, and a detector configured to detect light scattered or reflected from the object.

The object may include at least one of water not containing the target component, a solution that mimics a scattering coefficient of the target component, and human skin.

The processor may be further configured to obtain a change in absorbance with respect to the temperature change based on the spectrum corresponding to the temperature change, and obtain the effective optical pathlength vectors corresponding to the temperature change based on a relationship between the obtained change in absorbance and a change in optical pathlength.

The processor may be further configured to obtain the change in absorbance corresponding to each wavelength based on the temperature change by Monte Carlo (MC) simulation.

Based on a relationship of a sum of a first value, obtained by multiplying the change in absorbance, a change in an absorption coefficient, and an optical pathlength, and a second value obtained by multiplying the absorption coefficient and the change in optical pathlength, the processor may be further configured to obtain the effective optical pathlength vectors corresponding to the temperature change.

The processor may be further configured to obtain the first value at an isosbestic wavelength based on a change in absorbance, and obtain the effective optical pathlength vectors for each wavelength based on the change in absorbance at another wavelength and a change in the first value and a change in the second value.

The processor may be further configured to obtain the second value for each wavelength based on a lookup table or a pre-defined model equation.

The processor may be further configured to obtain a value, including an average value of the effective optical pathlength vectors for each wavelength, as the representative effective optical pathlength.

The processor may be further configured to obtain the target component estimation model based on at least one of least squares and net analyte signal (NAS) based on the obtained representative effective optical pathlength.

The processor may be further configured to obtain the target component including at least one of blood glucose, calories, alcohol, triglyceride, protein, cholesterol, uric acid, and carotenoid, based on the spectrum of the object being measured.

According to another aspect of an example embodiment, there is provided a method of estimating a target component, the method including modulating temperature of an object, obtaining a spectrum for each temperature that changes based on the modulation, obtaining effective optical pathlength vectors corresponding to a temperature change based on the spectrum for each temperature, obtaining a representative effective optical pathlength based on the obtained effective optical pathlength vectors, and obtaining a target component estimation model based on the obtained representative effective optical pathlength.

The modulating of the temperature of the object may include performing modulation one or more times within a predetermined temperature range.

The obtaining of the effective optical pathlength vectors corresponding to the temperature change may include obtaining a change in absorbance with respect to the temperature change based on the spectrum corresponding to the temperature change, and obtaining the effective optical pathlength vectors corresponding to the temperature change based on a relationship between the obtained change in absorbance and a change in optical pathlength.

The obtaining of the effective optical pathlength vectors corresponding to the temperature change may include obtaining the effective optical pathlength vectors corresponding to the temperature change, based on a relationship of a sum of a first value, obtained by multiplying the change in absorbance, a change in an absorption coefficient, and an optical pathlength, and a second value obtained by multiplying the absorption coefficient and the change in optical pathlength.

The obtaining of the effective optical pathlength vectors corresponding to the temperature change may include obtaining the first value at an isosbestic wavelength based on the change in absorbance, and obtaining the effective optical pathlength vectors for each wavelength based on a change in absorbance at another wavelength and a change in the first value and a change in the second value.

The obtaining of the representative effective optical pathlength may include obtaining a value, including an average value of the effective optical pathlength vectors for each wavelength, as the representative effective optical pathlength.

The method may further include obtaining the target component based on the measured spectrum and the target component estimation model based on the spectrum being measured from the object.

BRIEF DESCRIPTION OF THE DRAWINGS

The above and other aspects, features, and advantages of example embodiments of the disclosure will be more apparent from the following description taken in conjunction with the accompanying drawings, in which.

DETAILED DESCRIPTION

Figure 1:
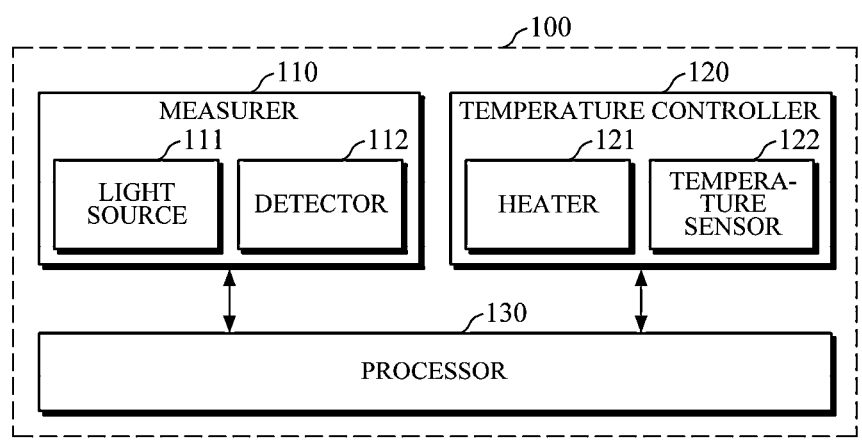
FIG. 1 is a block diagram illustrating an apparatus for estimating a target component according to an example embodiment.

Details of example embodiments are included in the following detailed description and drawings. Advantages and features of the present disclosure, and a method of achieving the same will be more clearly understood from the following example embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. It will be further understood that when an element is referred to as "comprising" another element, the element is intended not to exclude one or more other elements, but to further include one or more other elements, unless explicitly described to the contrary. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c. In the following description, terms such as "unit" and "module" indicate a unit for processing at least one function or operation and they may be implemented by using hardware, software, or a combination thereof.

Hereinafter, example embodiments of an apparatus and method for estimating a target component will be described in detail with reference to the accompanying drawings.

Various example embodiments of the apparatus for estimating a target component may be mounted in various information processing devices, such as a portable wearable device, a smart device, and the like. Examples of various information processing devices may include various types of wearable devices, such as a smart watch worn on the wrist, a smart band-type wearable device, a headphone-type wearable device, a hairband-type wearable device, etc., or a mobile device, such as a smartphone, a tablet PC, etc., or a system of a specialized medical institution, and the like. However, the information processing devices are not limited thereto.

FIG. 1 is a block diagram illustrating an apparatus for estimating a target component according to an example embodiment.

Referring to FIG. 1, the apparatus 100 for estimating a target component includes a measurer 110, a temperature controller 120, and a processor 130.

The measurer 110 may calibrate a target component estimation model, or may measure a spectrum from an object for estimating a target component. In this case, the object for estimating a target component may be body tissue containing a target component to be analyzed, e.g., human skin tissue, such as an upper portion of the wrist which is adjacent to the radial artery, or veins or capillaries are located, fingers, and the like. Further, in the case where a target component estimation model is calibrated, the object may include water containing no target component, or a solution that mimics a scattering coefficient of a target component, human skin, and the like. In this case, the target component may include at least one of blood glucose, calories, alcohol, triglyceride, protein, cholesterol, uric acid, and carotenoid, but is not limited thereto.

The measurer 110 may include one or more light sources 111 for emitting light onto the object, and a detector 112 for detecting light scattered or reflected from the object. The light source 111 may be formed as a light emitting diode (LED), a laser diode (LD), a phosphor, or a combination thereof. In addition, the light sources may be formed as an array of a plurality of light sources such that the respective light sources may emit light of different wavelengths. The detector 112 may be formed as a photo diode, a photo transistor (PTr), or an array thereof. However, embodiments are not limited thereto. For example, the detector 112 may be formed as an image sensor, for example, complementary metal-oxide semiconductor (CMOS) image sensor, and the like.

The temperature controller 120 may modulate temperature of the object while the measurer 110 measures a spectrum from the object. The temperature controller 120 may include a heater 121 and a temperature sensor 122. The heater 121 may provide thermal energy to the object for temperature modulation of the object, and the temperature sensor 122 may measure temperature of the object which is changed by the thermal energy provided by the heater 121.

The heater 121 and the temperature sensor 122 may interact with each other to modulate temperature of the object at least once within a predetermined temperature range. For example, when performing modulation a plurality of number of times, the temperature controller 120 may perform a second modulation successively as soon as a first modulation ends, so that each time modulation is performed, temperature of the object may increase continuously within a predetermined temperature range.

Further, temperature modulation may be performed at a calibration time and/or a target component estimation time. For example, the temperature modulation may be performed only at a calibration time of the object, without being performed at the target component estimation time.

According to the example embodiment, the measurer 110 and the temperature controller 120 may be integrally formed with one hardware device, but embodiments are not necessarily limited thereto. For example, the measurer 110 and the temperature controller 120 may be formed as separate devices.

The processor 130 may be electrically connected to the measurer 110 and the temperature controller 120, and may control the measurer 110 and the temperature controller 120.

The processor 130 may control temperature controller 120, may obtain a spectrum for each temperature from an object for calibration, which is measured by the measurer 110 according to the modulation performed by the temperature controller 120, and may generate and/or calibrate a target component estimation model based on the obtained spectrum for each temperature.

For example, the processor 130 may obtain effective optical pathlength vectors from the object according to a temperature change based on the spectrum for each temperature, and may obtain a representative optical pathlength from the obtained effective optical pathlength vectors.

Figure 2:
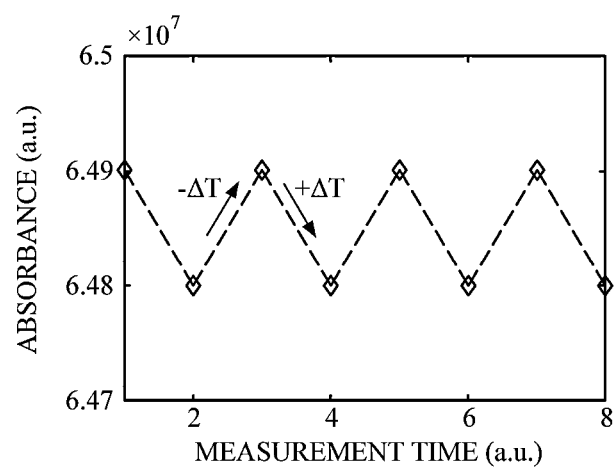
FIG. 2 is a diagram illustrating a change in absorbance according to a temperature change, according to an example embodiment.

For example, as illustrated in FIG. 2, as the temperature controller 120 applies a temperature change to the object, the absorbance of the object changes.

A change in absorbance $\partial A$ with respect to a temperature change has a relationship with a first value $l_{eff}*\partial \mu_a$ and a second value $\mu_a*\partial l_{eff}$, as represented by the following Equation 1, in which $l_{eff}$ denotes the effective optical pathlength, $\mu_a$ denotes the absorption coefficient, $\partial l_{eff}$ denotes a change in effective optical pathlength, and $\partial \mu_a$ denotes a change in absorption coefficient.

$$\partial A = l_{eff}\partial \mu_a + \mu_a \partial l_{eff} \qquad \text{[Equation 1]}$$

Figure 3A:
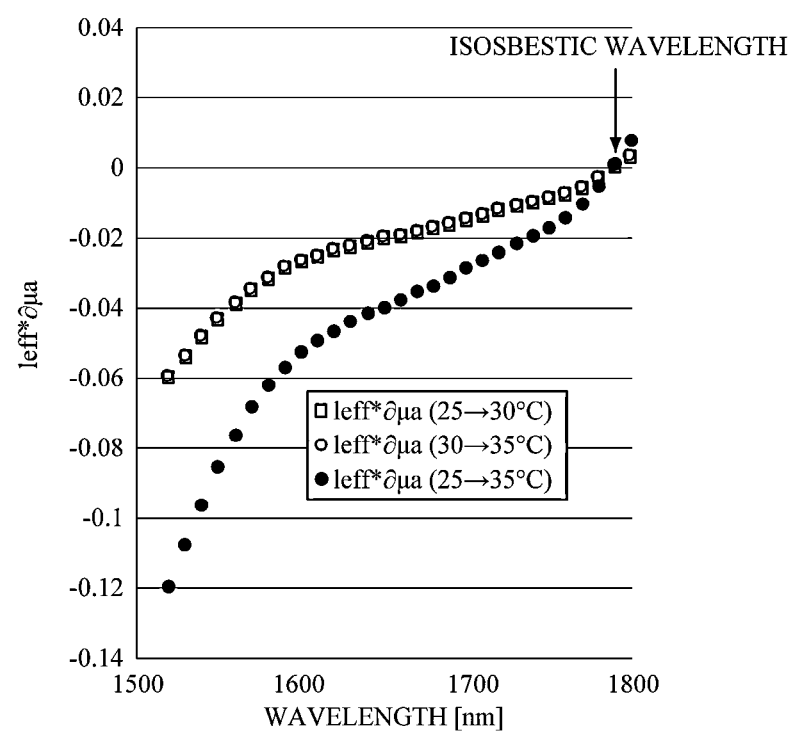
FIGS. 3A and 3B are diagrams illustrating a first value $l_{eff}*\partial\mu_a$ and a second value $\mu_a*\partial l_{eff}$ for each wavelength according to a temperature change by Monte Carlo (MC) simulation.
Figure 3B:
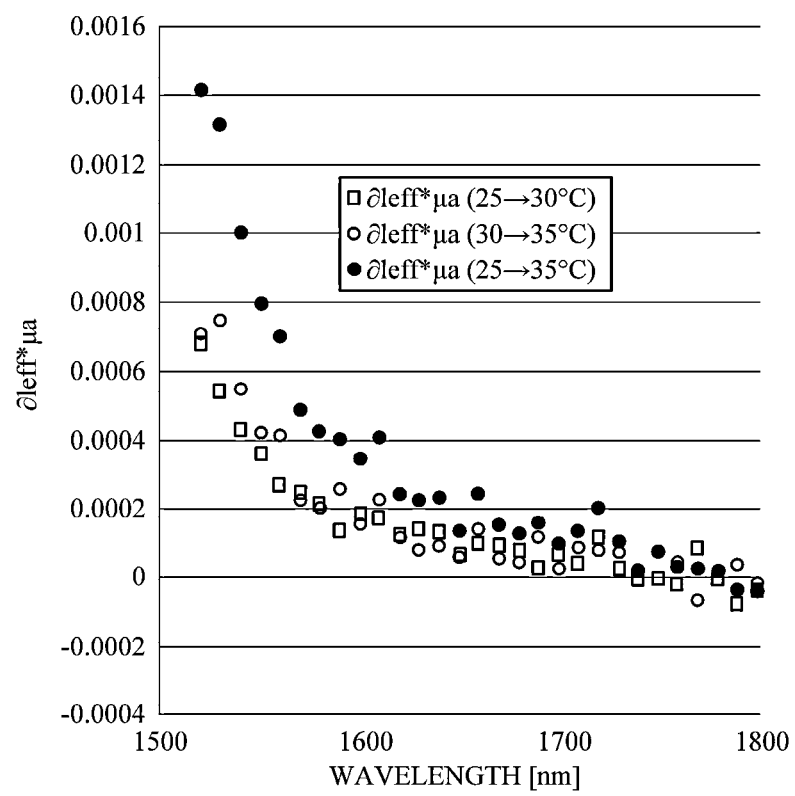

FIG. 3A is a diagram illustrating a variation in the first value $l_{eff}*\partial \mu_a$ for each wavelength according to a temperature change by Monte Carlo (MC) simulation. FIG. 3B is a diagram illustrating a variation in the second value $\mu_a*\partial l_{eff}$ for each wavelength according to a temperature change by Monte Carlo (MC) simulation.

For example, the processor 130 may obtain effective optical pathlength vectors according to a temperature change by using the first value $l_{eff}*\partial \mu_a$. Referring to FIGS. 3A and 3B, a simulation result shows that the first value $l_{eff}*\partial \mu_a$ is several hundred times greater than the second value $\mu_a*\partial l_{eff}$, such that the second value may be ignored, and thus Equation 1 may be approximated, as shown in the following Equation 2.

$$\partial A \approx l_{eff}\partial \mu_a \qquad \text{[Equation 2]}$$

In Equation 2, an absorption coefficient change $\partial \mu_a$ corresponds to intrinsic properties of a material that never change, such that by using a variation in absorbance which corresponds to the calculated first value $l_{eff}*\partial \mu_a$, the effective optical pathlength vector may be obtained.

In another example embodiment, the second value $\mu_a*\partial l_{eff}$ may be obtained for each wavelength based on a lookup table or a pre-defined model equation. A change in absorbance with respect to a temperature change may be expressed in Equation 1, in which $\partial \mu_a = 0$ at an isosbestic wavelength shown in FIG. 3A, and thus may be approximated as shown in the following Equation 3.

$$\partial A \approx l_{eff}\partial \mu_a + \mu_a \partial l_{eff} \approx \mu_a \partial l_{eff} \qquad \text{[Equation 3]}$$

The processor 130 may first perform fitting of the second value $\mu_a*\partial l_{eff}$ by using the absorbance change $\partial A$ at the isosbestic wavelength, and may obtain the effective optical pathlength vector based on the absorbance change and the change in the first value $l_{eff}*\partial \mu_a$ and the second value $\mu_a*\partial l_{eff}$. Referring to FIG. 3A, the isosbestic wavelength may be, for example, approximately 1780 nm.

Referring back to FIG. 1, the processor 130 may determine a representative effective optical pathlength based on the obtained effective optical pathlength vectors for each wavelength.

For example, the processor 130 may determine an average value of the effective optical pathlength vectors for each wavelength to be the representative effective optical pathlength. However, the representative effective optical pathlength is not limited thereto, and the processor 130 may also determine a statistical value, such as a median value, a maximum value, a minimum value, etc., or a value obtained by combining the vectors using a pre-defined combination equation, to be the representative effective optical pathlength.

Figure 4:
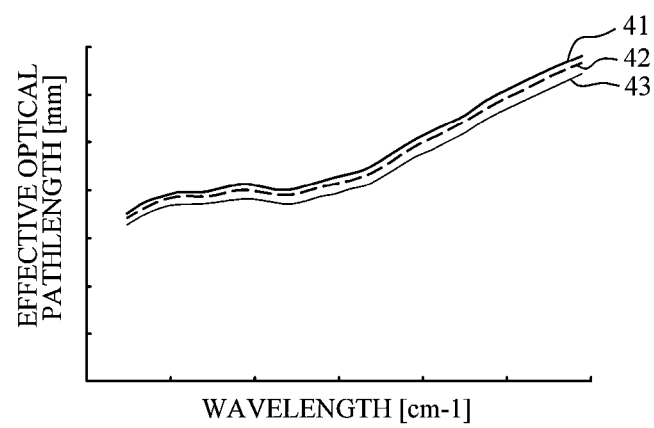
FIG. 4 is a diagram illustrating effective optical pathlength vectors for each wavelength and an average value thereof.

FIG. 4 is a diagram illustrating effective optical pathlength vectors for each wavelength and an average value thereof.

For example, the processor 130 may determine, as the representative effective optical pathlength, a value 42 corresponding to an average value of effective optical pathlength vectors 41 for each wavelength according to a temperature change in a range of 30° C. to 35° C. and effective optical pathlength vectors 43 for each wavelength according to a temperature change in a range of 25° C. to 35° C.

Referring back to FIG. 1, the processor 130 may generate a target component estimation model by using the determined representative effective optical pathlength.

By applying the determined representative effective optical pathlength to a model based on at least one of least squares and net analyte signal (NAS), the processor 130 may generate or calibrate a target component estimation model, but the processor 130 is not limited thereto.

Figure 5A:
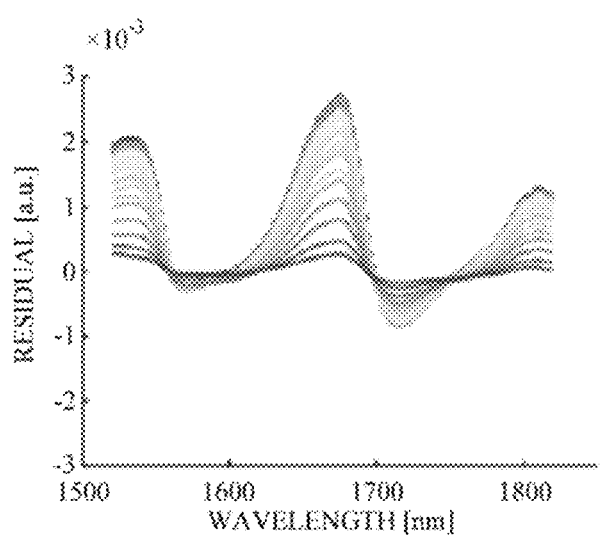
FIGS. 5A and 5B are diagrams illustrating a change in residual component before and after calibration of the target component estimation model using a representative effective optical pathlength.
Figure 5B:
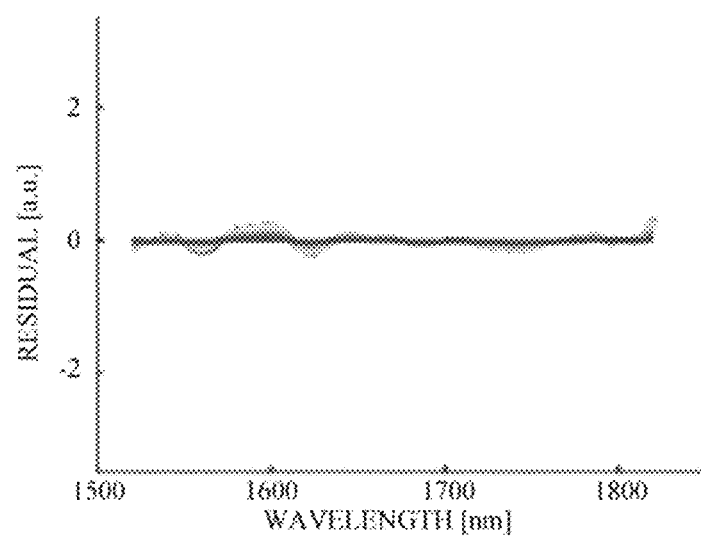

FIGS. 5A and 5B are diagrams illustrating a change in residual component before and after calibration of the target component estimation model using the representative effective optical pathlength.

Quantitative analysis of the object based on the Beer-Lambert law has a limitation in that it assumes optical pathlength distribution at all wavelengths is equal.

$$S = \varepsilon_w L C_w + \varepsilon_k L C_k + \varepsilon_c L C_c + \varepsilon_f L C_f + \varepsilon_g L C_g + \text{Residual} \quad \text{[Equation 4]}$$

That is, as represented by Equation 4, a linear regression equation using least squares, as a general model for estimating a target component, is a quantification method based on the assumption that a spectrum has linearity by combining an intrinsic absorption coefficient ε, derived from physical properties and a molecular structure of components included in a spectrum, a fixed optical pathlength L, and concentrations of the respective components.

Herein, S denotes a skin absorbance spectrum; $\varepsilon_w$, $\varepsilon_k$, $\varepsilon_c$, $\varepsilon_f$, and $\varepsilon_g$ denote absorption coefficients of water, keratin, collagen, fat, and glucose, respectively; and $C_w$, $C_k$, $C_c$, $C_f$, and $C_g$ denote concentrations of water, keratin, collagen, fat, and glucose, respectively.

As illustrated in FIG. 5A, if a linear regression equation is applied based on the assumption that an optical pathlength distribution is equal, it can be seen that a blood glucose measurement error may not be explained by the combination using the linear regression equation, but the blood glucose measurement error occurs in a range of, for example, 10 mg/dl to 1000 mg/dl, which is a range much greater than a normal blood glucose range of 80 mg/dl to 180 mg/dl for ordinary people.

$$S = \varepsilon_w l_{\textit{eff}} C_w + \varepsilon_k l_{\textit{eff}} C_k + \varepsilon_c l_{\textit{eff}} C_c + \varepsilon_f l_{\textit{eff}} C_f + \varepsilon_g l_{\textit{eff}} C_g + \text{Residual}$$

Equation 5 is an example of a target component estimation model used for calibrating an optical path with the obtained representative effective optical pathlength $l_{\textit{eff}}$, as described above according to an example embodiment.

As illustrated in FIG. 5B, when a target component estimation model is generated by least squares by obtaining the effective optical pathlength vectors, rather than a uniform optical pathlength distribution as shown in Equation 5, a variation in residual component is small, such that a target component may be more estimated accurately.

Referring back to FIG. 1, upon receiving a request for estimating a target component from a user or an external device, the processor 130 may control the measurer 110, and upon receiving a spectrum for measurement from the measurer 110, the processor 130 may estimate a target component by using a target component estimation model.

If there is a pre-defined calibration cycle or a user's request, the processor 130 may determine whether to perform calibration again by analyzing a target component estimation result, and upon determining that calibration is required, the processor 130 may guide a user to perform calibration again, and may control the measurer 110 and the temperature controller 120 to perform calibration by modulation for each temperature, as described above.

Figure 6:
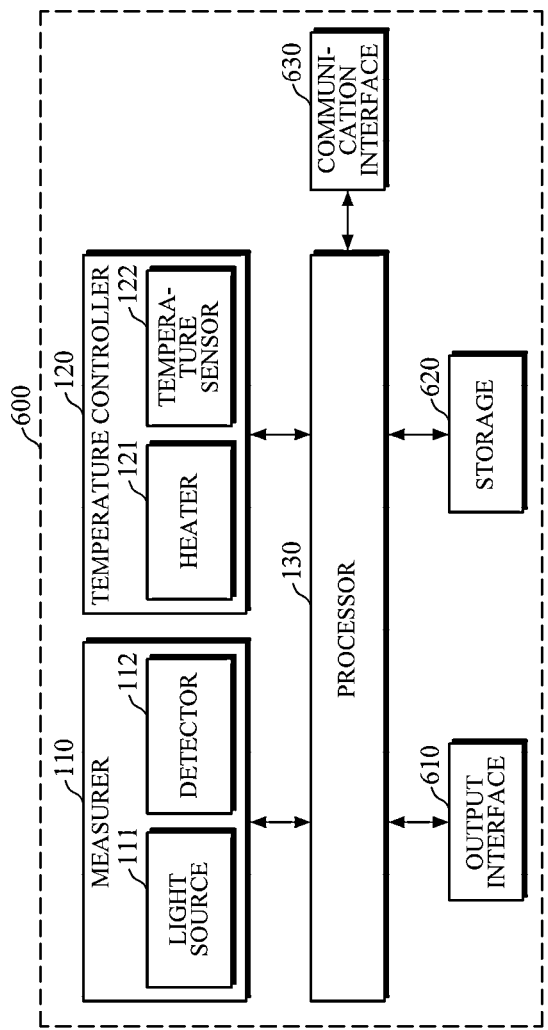
FIG. 6 is a block diagram illustrating an apparatus for estimating a target component according to another example embodiment.

FIG. 6 is a block diagram illustrating an apparatus for estimating a target component according to another example embodiment.

Referring to FIG. 6, the apparatus 600 for estimating a target component includes the measurer 110, the light source 111, the detector 112, the temperature controller 120, the heater 121, the temperature sensor 122, the processor 130, an output interface 610, a storage 620, and a communication interface 630. In this case, the measurer 110, the light source 111, the detector 112, the temperature controller 120, the heater 121, the temperature sensor 122, and the processor 130 are described above in detail with reference to FIG. 1, such that the following description will focus on non-overlapping parts.

The output interface 610 may output a variety of information processed by the processor 130. The output interface 610 may include a visual output module such as a display and the like, an audio output module such as a speaker and the like, or a haptic module using vibrations, tactile sensation, and the like. For example, the output interface 610 may generate a target component estimation model and/or may output a calibration result, and may output an estimation result of a target component estimated by using the generated and/or calibrated target component estimation model.

The storage 620 may store user characteristic information, driving condition information of the light source 111 and the detector 112 of the measurer 110, and the like. Further, the storage 620 may store processing results of the processor 130, for example, effective optical pathlength vector information according to a temperature change, information on the determined representative effective optical pathlength, the generated and/or calibrated target component estimation model, the estimation result of the target component estimated by using the generated and/or calibrated target component estimation model.

The storage 620 may include at least one storage medium of a flash memory type memory, a hard disk type memory, a multimedia card micro type memory, a card type memory (e.g., an SD memory, an XD memory, etc.), a random access memory (RAM), a static random access memory (SRAM), a read only memory (ROM), an electrically erasable programmable read only memory (EEPROM), a programmable read only memory (PROM), a magnetic memory, a magnetic disk, and an optical disk, and the like, but is not limited thereto.

The communication interface 630 may communicate with an external device through wired or wireless communications to receive a variety of information from the external device. The external device may include an information processing device such as a smartphone, a tablet personal computer (PC), a laptop computer, a desktop computer, and the like, but is not limited thereto, and may have a function of estimating a component of an object.

For example, the communication interface 630 may receive, from an external device, a request for generating and/or calibrating a target component estimation model for estimating a target component of an object, and may transmit the request to the processor 130. Further, the communication interface 630 may receive, from the external device, a request for estimating a target component, which is to be performed by using the generated and/or calibrated target component estimation model, and may transmit the request to the processor 130.

In this case, in response to the request, the processor 130 may control the measurer 110. Further, by receiving reference information, such as driving conditions of the light source 111 and the detector 112 and the like, from the external device, the communication interface 630 may transmit the reference information to the processor 130. In this case, the processor 130 may store the received reference information in the storage 62. In addition, the communication interface 630 may transmit processing results of the processor 130 to the external device.

The communication interface 630 may communicate with the external device by using various wired or wireless communication techniques, such as Bluetooth communication, Bluetooth Low Energy (BLE) communication, near field communication (NFC), WLAN communication, Zigbee communication, infrared data association (IrDA) communication, Wi-Fi Direct (WFD) communication, ultra-wideband (UWB) communication, Ant+ communication, WIFI communication, radio frequency identification (RFID) communication, 3G communication, 4G communication, 5G communication, and the like. However, embodiments of the communication techniques are not limited thereto.

Figure 7:
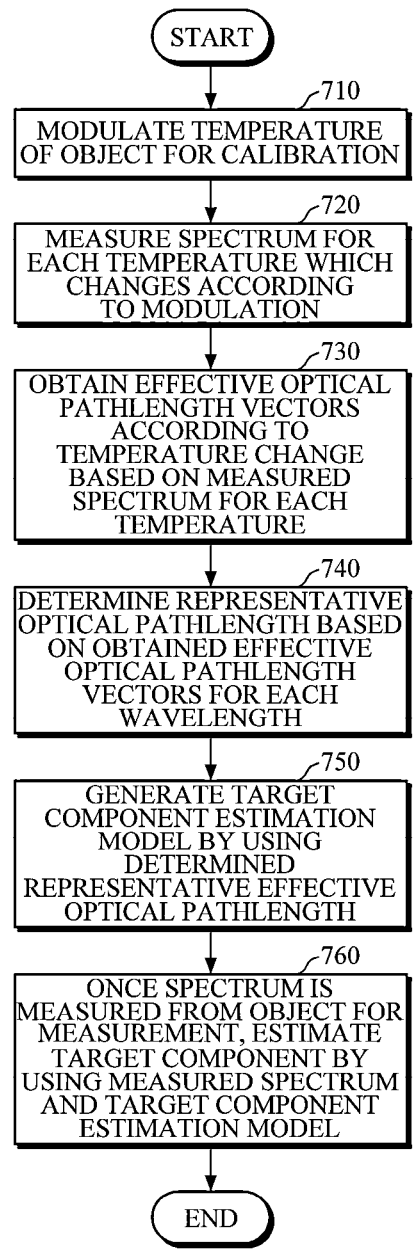
FIG. 7 is a flowchart illustrating a method of estimating a target component according to an example embodiment.

FIG. 7 is a flowchart illustrating a method of estimating a target component according to an example embodiment.

Referring to FIG. 7, the apparatus for estimating a target component may modulate temperature of an object for calibration in operation 710. The object for calibration of a target component estimation model may include water containing no target component, or a solution that mimics a scattering coefficient of a target component, human skin, and the like.

Temperature modulation of the object may be performed at least one or more times within a predetermined temperature range by interaction between the heater 121 and the temperature sensor 122.

For example, if modulation is performed a plurality of number of times, the apparatus for estimating a target component may perform a second modulation successively as soon as a first modulation ends, so that each time modulation is performed, temperature of the object may increase continuously within a predetermined temperature range.

Then, the apparatus for estimating a target component may measure a spectrum for each temperature which changes according to the temperature modulation in operation 720. For example, the apparatus for estimating a target component may measure a spectrum for each temperature by using one or more light sources 111 emitting light onto an object, and the detector 112 detecting light scattered or reflected from the object. The light source 111 may be formed as a light emitting diode (LED), a laser diode (LD), a phosphor, or a combination thereof. In addition, the light source may be formed as an array of a plurality of light sources such that the respective light sources may emit light of different wavelengths. The detector 112 may be formed as a photo diode, a photo transistor (PTr), or an array thereof. Alternatively, the detector 112 may be formed as an image sensor, e.g., complementary metal-oxide semiconductor (CMOS) image sensor and the like.

Subsequently, the apparatus for estimating a target component may obtain effective optical pathlength vectors according to a temperature change based on the measured spectrum for each temperature in operation 730.

For example, the apparatus for estimating a target component may calculate a change in absorbance with respect to a temperature change based on a spectrum according to the temperature change, and may obtain effective optical pathlength vectors according to the temperature change based on a relationship between the calculated change in absorbance and a change in optical pathlength.

In addition, as described above using Equation 1, based on a relationship of a sum of a first value, obtained by multiplying the change in absorbance, a change in absorption coefficient, and an optical pathlength, and a second value obtained by multiplying an absorption coefficient and a change in optical pathlength, the apparatus for estimating a target component may obtain effective optical pathlength vectors according to a temperature change.

For example, when a variation in the first value for each wavelength according to a temperature change and a variation in the second value for each wavelength according to a temperature change are calculated by Monte Carlo (MC) simulation, the simulation result shows that the first value is several hundred times greater than the second value, such that the second value may be ignored, and thus the effective optical pathlength vectors may be obtained by using the calculated variation in absorbance which corresponds to the first value.

In another example, the apparatus for estimating a target component may calculate a first value at an isosbestic wavelength based on the change in absorbance, and may obtain effective optical pathlength vectors for each wavelength based on a change in absorbance at another wavelength and the change in the first and second values. Here, the second value may be obtained based on a lookup table or a pre-defined model equation.

When the second value may be obtained for each wavelength based on the lookup table or the pre-defined model equation, the apparatus for estimating a target component may first perform fitting of the second value using the change in absorbance at the isosbestic wavelength and may obtain the effective optical pathlength vectors based on the change in absorbance at another wavelength and the change in the first and second values.

Then, the apparatus for estimating a target component may determine a representative optical pathlength based on the obtained effective optical pathlength vectors for each wavelength in operation 740. For example, the apparatus for estimating a target component may determine an average value of the effective optical pathlength vectors to be the representative effective optical pathlength. However, the representative effective optical pathlength is not limited thereto, and the apparatus for estimating a target component may determine a statistical value, such as a median value, a maximum value, a minimum value, etc., or a value obtained by combining the vectors using a pre-defined combination equation, to be the representative effective optical pathlength.

Subsequently, the apparatus for estimating a target component may generate a target component estimation model by using the determined representative effective optical pathlength in operation 750. For example, by applying the determined representative effective optical pathlength to a model based on at least one of least square and net analyte signal (NAS), the apparatus for estimating a target component may generate and/or calibrate a target component estimation model. However, the target component estimation model is not limited thereto.

As described above, in the case where a target component estimation model is generated by obtaining the effective optical pathlength vectors, rather than using a uniform optical pathlength distribution, a variation in residual component is relatively small, such that a target component may be estimated more accurately.

Next, once the spectrum is measured from the object for measurement, the apparatus for estimating a target component may estimate a target component by using the measured spectrum and the target component estimation model in operation 760.

Figure 8:
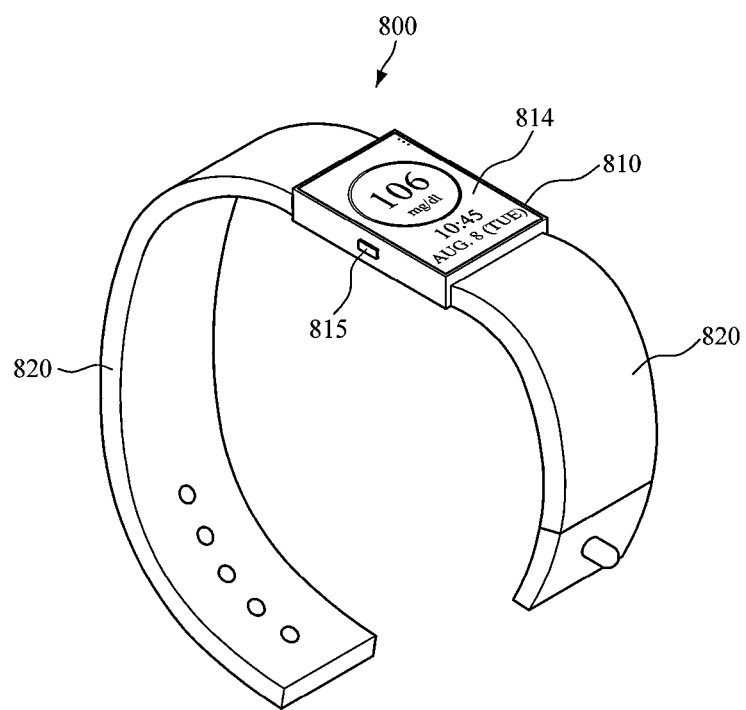
FIG. 8 is a diagram illustrating a structure of an electronic device including an apparatus for estimating a target component according to an example embodiment.

FIG. 8 is a diagram schematically illustrating an example of an electronic device including an apparatus for estimating a target component according to an example embodiment.

As illustrated in FIG. 8, an example embodiment of the electronic device may be a smart watch-type wearable device 800, but is not particularly limited to a specific type, and may include various types of wearable devices, such as a smartphone, a tablet PC, a smart band, smart earphones, a smart ring, a smart necklace, and the like. The wearable device 800 of FIG. 8 may have a function of generating and/or calibrating the aforementioned target component estimation model, and a function of estimating a target component by using the generated and/or calibrated target component estimation model.

Referring to FIG. 8, the wearable device 800 includes a main body 810 and a strap 820.

The strap 820, which is connected to both ends of the main body 810, may be flexible so as to be wrapped around a user's wrist. The strap 820 may be composed of a first strap and a second strap which are separated from each other. One ends of the first strap and the second strap are connected to the main body 810, and the other ends thereof may be connected to each other via a connecting means. In this case, the connecting means may be formed as magnetic connection, Velcro connection, pin connection, and the like, but is not limited thereto. Further, the strap 820 is not limited thereto, and may be integrally formed as a non-detachable band. In this case, air may be injected into the strap 820, or the strap 820 may be provided with an air bladder to have elasticity according to a change in pressure applied to the wrist, and may transmit the change in pressure of the wrist to the main body 810.

In this case, a battery may be embedded in the main body 810 or the strap 820 to supply power to the wearable device 800.

In addition, the apparatuses 100 or 600 for estimating a target component may be mounted in the main body 810. The apparatuses 100 or 600 for estimating a target component may include the measurer 110, the temperature controller 120, and the processor 130, as described above with reference to FIGS. 1 to 6. The measurer 110 may include the light source 111 for emitting light of one or more wavelengths onto an object (e.g., a user's wrist or finger), and the detector 112 for detecting light scattered or reflected from the object. The temperature controller 120 may include the heater 121 for providing thermal energy to the object, and the temperature sensor 122 for measuring a change in temperature of the object. The processor 130 controls the temperature controller 120, and obtains a spectrum for each temperature from the object for calibration which is measured by the measurer 110 according to modulation performed by the temperature controller 120, and may generate and/or calibrate a target component estimation model based on the obtained spectrum for each temperature. For example, by obtaining effective optical pathlength vectors from the object according to the temperature change based on the spectrum for each temperature and by obtaining a representative optical pathlength from the obtained effective optical pathlength vectors, the processor 130 may generate a target component estimation model by using the representative optical pathlength. Once the spectrum for estimating a target component is obtained from the object, the processor 130 may estimate a target component by using the target component estimation model.

A display, provided on a front surface of the main body 810, may display various application screens, including time information, received message information, and the like. A rear surface of the main body 810 may come into contact with the upper part of a user's wrist.

Further, the wearable device 800 may further include a manipulation interface 815 and a display unit 814 which are mounted in the main body 810. The manipulation interface 815 may receive and transmit a user command, and may have a power button to input a command to turn on/off the wearable device 800. The display unit 814 may display additional information, such as a component estimation result, warning, alarm, etc., by various visual methods to provide the information to the user.

Embodiments can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing the present invention can be readily deduced by programmers of ordinary skill in the art.

While example embodiments have been illustrated and described above, it will be apparent to those skilled in the art that modifications and variations could be made without departing from the scope as defined by the appended claims and their equivalents.

What is claimed is:

1. An apparatus for estimating a target component, the apparatus comprising:
   a temperature controller configured to modulate temperature of an object;
   a measurer configured to measure a spectrum for each temperature of the object that changes based on the modulation; and
   a processor configured to:
      obtain effective optical pathlength vectors corresponding to a temperature change based on the spectrum for each temperature of the object;
      obtain a representative effective optical pathlength based on the obtained effective optical pathlength vectors; and
      obtain a target component estimation model based on the obtained representative effective optical pathlength,
   wherein the processor is further configured to:
      obtain a change in absorbance with respect to the temperature change based on the spectrum corresponding to the temperature change; and
      obtain the effective optical pathlength vectors corresponding to the temperature change based on a relationship between the obtained change in absorbance and a change in optical pathlength, a change in absorbance being proportional to a sum of the effective optical pathlength multiplied by the change in an absorption coefficient and the absorption coefficient multiplied by a change in the effective optical pathlength.

2. The apparatus of claim 1, wherein the temperature controller comprises:
   a heater configured to provide thermal energy to the object; and
   a temperature sensor configured to measure the temperature change of the object.

3. The apparatus of claim 2, wherein the temperature controller is further configured to perform the modulation one or more times within a predetermined temperature range.

4. The apparatus of claim 1, wherein the measurer comprises:

one or more light sources configured to emit light of one or more wavelengths to the object; and a detector configured to detect light scattered or reflected from the object.

5. The apparatus of claim 1, wherein the object comprises at least one of water not containing the target component, a solution that mimics a scattering coefficient of the target component, and human skin.

6. The apparatus of claim 1, wherein the processor is further configured to obtain the change in absorbance corresponding to a wavelength based on the temperature change by Monte Carlo (MC) simulation.

7. The apparatus of claim 1, wherein the processor is further configured to:

obtain a first value based on the change in absorbance at an isosbestic wavelength, the first value being the effective optical pathlength multiplied by the change in the absorption coefficient; and obtain the effective optical pathlength vectors for a plurality of wavelengths based on the change in absorbance at another wavelength and a change in the first value and a change in a second value being the absorption coefficient multiplied by the change in the effective optical pathlength.

8. The apparatus of claim 7, wherein the processor is further configured to obtain the second value for each wavelength based on a lookup table or a pre-defined model equation.

9. The apparatus of claim 1, wherein the processor is further configured to obtain a value, including an average value of the effective optical pathlength vectors for a plurality of wavelengths, as the representative effective optical pathlength.

10. The apparatus of claim 1, wherein the processor is further configured to obtain the target component estimation model based on at least one of least squares and net analyte signal (NAS) based on the obtained representative effective optical pathlength.

11. The apparatus of claim 1, wherein the processor is further configured to obtain the target component including at least one of blood glucose, calories, alcohol, triglyceride, protein, cholesterol, uric acid, and carotenoid, based on the spectrum for each temperature of the object being measured.

12. A method of estimating a target component, the method comprising:

modulating temperature of an object;

obtaining a spectrum for each temperature that changes based on the modulation;

obtaining effective optical pathlength vectors corresponding to a temperature change based on the spectrum for each temperature;

obtaining a representative effective optical pathlength based on the obtained effective optical pathlength vectors; and obtaining a target component estimation model based on the obtained representative effective optical pathlength, wherein the obtaining of the effective optical pathlength vectors corresponding to the temperature change comprises:

obtaining a change in absorbance with respect to the temperature change based on the spectrum corresponding to the temperature change, and obtaining the effective optical pathlength vectors corresponding to the temperature change based on a relationship between the obtained change in absorbance and a change in optical pathlength, a change in absorbance being proportional to a sum of the effective optical pathlength multiplied by the change in an absorption coefficient and the absorption coefficient multiplied by a change in the effective optical pathlength.

13. The method of claim 12, wherein the modulating of the temperature of the object comprises performing the modulation one or more times within a predetermined temperature range.

14. The method of claim 12, wherein the obtaining of the effective optical pathlength vectors corresponding to the temperature change comprises obtaining a first value based on the change in absorbance at an isosbestic wavelength, and obtaining the effective optical pathlength vectors for wavelengths based on the change in absorbance at another wavelength and a change in the first value and a change in a second value.

15. The method of claim 12, wherein the obtaining of the representative effective optical pathlength comprises obtaining a value, including an average value of the effective optical pathlength vectors for a plurality of wavelengths, as the representative effective optical pathlength.

16. The method of claim 12, further comprising obtaining the target component based on the measured spectrum and the target component estimation model based on the spectrum being measured from the object.

* * * * *